US012389948B2

(12) United States Patent
Hejazi

(10) Patent No.: US 12,389,948 B2
(45) Date of Patent: *Aug. 19, 2025

(54) AEROSOL DELIVERY DEVICE WITH DUAL RESERVOIR

(71) Applicant: RAI Strategic Holdings, Inc., Winston-Salem, NC (US)

(72) Inventor: Vahid Hejazi, Concord, NC (US)

(73) Assignee: RAI STRATEGIC HOLDINGS, INC., Winston-Salem, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 18/663,775

(22) Filed: May 14, 2024

(65) Prior Publication Data
US 2024/0292897 A1 Sep. 5, 2024

Related U.S. Application Data

(63) Continuation of application No. 17/699,805, filed on Mar. 21, 2022, now Pat. No. 12,011,042, which is a
(Continued)

(51) Int. Cl.
*A24F 13/00* (2006.01)
*A24F 40/30* (2020.01)
(Continued)

(52) U.S. Cl.
CPC .............. *A24F 40/46* (2020.01); *A24F 40/30* (2020.01); *A61M 15/0085* (2013.01); *A61M 15/06* (2013.01); *B05B 17/0676* (2013.01)

(58) Field of Classification Search
CPC ...................................... A24F 47/00
(Continued)

(56) References Cited

U.S. PATENT DOCUMENTS 5,996,903 A 12/1999 Asai et al.
8,998,483 B2 4/2015 Friend et al.
(Continued)

FOREIGN PATENT DOCUMENTS

CN 206423575 8/2017
EP 3228345 10/2017
(Continued)

OTHER PUBLICATIONS

Ding et al., "Surface acoustic wave microfluidics", The Royal Society of Chemistry, Issue 18, Jul. 2013, pp. 3626-3649. Retrieved from the Internet: <DOI: 10.1039/c31c5036le>.
(Continued)

*Primary Examiner* — Phuong K Dinh
(74) *Attorney, Agent, or Firm* — Womble Bond Dickinson (US) LLP

(57) ABSTRACT

The present disclosure provides an aerosol delivery device that comprises a housing defining an outer wall, and further including a power source and a control component, a mouthpiece portion that defines an aerosol exit path, a first reservoir configured to contain a first liquid composition, a second reservoir configured to contain a second liquid composition, a first atomization assembly configured to vaporize the first liquid composition to generate a first aerosol having a first aerosol particle size, and a second atomization assembly configured to vaporize the second liquid composition to generate a second aerosol having a second aerosol particle size. The first liquid composition may be different than the second liquid composition, and the first particle size may be different than the second particle size.

20 Claims, 5 Drawing Sheets

Related U.S. Application Data continuation of application No. 16/657,219, filed on Oct. 18, 2019, now Pat. No. 11,304,451.

(51) Int. Cl.
*A24F 40/46* (2020.01)
*A61M 15/00* (2006.01)
*A61M 15/06* (2006.01)
*B05B 17/06* (2006.01)

(58) Field of Classification Search
USPC .................................................. 131/328–329
See application file for complete search history.

(56) References Cited

U.S. PATENT DOCUMENTS

| | | |
|---|---|---|
| 9,770,055 B2 | 9/2017 | Cameron et al. |
| 9,848,648 B2 | 12/2017 | Memari et al. |
| 9,867,398 B2 | 1/2018 | Guo et al. |
| 9,936,737 B2 | 4/2018 | Cameron et al. |
| 10,004,259 B2 | 6/2018 | Sebastian et al. |
| 11,304,451 B2 * | 4/2022 | Hejazi ................... A24F 40/46 |
| 12,011,042 B2 * | 6/2024 | Hejazi ................... A24F 40/30 |
| 2006/0196518 A1 | 9/2006 | Hon |
| 2008/0084134 A1 | 4/2008 | Morita et al. |
| 2009/0151717 A1 | 6/2009 | Bowen et al. |
| 2013/0213419 A1 | 8/2013 | Tucker et al. |
| 2013/0319404 A1 | 12/2013 | Feriani et al. |
| 2014/0238423 A1 | 8/2014 | Tucker et al. |
| 2014/0261487 A1 | 9/2014 | Chapman et al. |
| 2014/0261488 A1 | 9/2014 | Tucker |
| 2015/0034103 A1 | 2/2015 | Hon |
| 2015/0101606 A1 | 4/2015 | White |
| 2015/0117841 A1 | 4/2015 | Brammer et al. |
| 2015/0238423 A1 | 8/2015 | Wertz et al. |
| 2015/0245669 A1 | 9/2015 | Cadieux et al. |
| 2016/0213866 A1 | 7/2016 | Tan |
| 2016/0271347 A1 | 9/2016 | Raichman |
| 2016/0366946 A1 | 12/2016 | Murison et al. |
| 2017/0042241 A1 | 2/2017 | Murison et al. |
| 2017/0064997 A1 | 3/2017 | Murison et al. |
| 2017/0157341 A1 | 6/2017 | Pandya et al. |
| 2017/0238608 A1 | 8/2017 | Matsumoto et al. |
| 2017/0251727 A1 | 9/2017 | Nielsen |
| 2017/0258140 A1 | 9/2017 | Rostami et al. |
| 2017/0303594 A1 | 10/2017 | Cameron et al. |
| 2017/0368273 A1 | 12/2017 | Rubin |
| 2018/0038838 A1 | 2/2018 | Karancsi et al. |
| 2018/0090923 A1 | 3/2018 | Li et al. |
| 2018/0153217 A1 | 6/2018 | Liu et al. |
| 2018/0161525 A1 | 6/2018 | Liu et al. |
| 2018/0169691 A1 | 6/2018 | MacLoughlin et al. |
| 2018/0228216 A1 | 8/2018 | Saygili |
| 2018/0289076 A1 | 10/2018 | Manca et al. |
| 2019/0014819 A1 | 1/2019 | Sur |
| 2019/0124982 A1 | 5/2019 | Atkins et al. |
| 2020/0268057 A1 | 8/2020 | Sahin et al. |
| 2020/0367553 A1 * | 11/2020 | Hejazi ................... A24F 40/10 |

FOREIGN PATENT DOCUMENTS

| | | |
|---|---|---|
| EP | 3272237 | 1/2018 |
| EP | 3278678 | 2/2018 |
| EP | 3287019 | 2/2018 |
| EP | 3298912 | 3/2018 |
| EP | 3305104 | 4/2018 |
| GB | 2566766 | 3/2019 |
| JP | 2019076101 | 5/2019 |
| KR | 20160003136 U | 9/2016 |
| KR | 201820835 B1 | 1/2018 |
| RU | 94815 | 6/2010 |
| WO | WO2016165055 | 10/2016 |
| WO | 2017021441 A1 | 2/2017 |
| WO | WO2017051181 | 3/2017 |
| WO | WO2017063256 | 4/2017 |
| WO | WO2017149165 | 9/2017 |
| WO | WO2017/185051 | 10/2017 |
| WO | WO2017175218 | 10/2017 |
| WO | WO2017201710 | 11/2017 |
| WO | WO2017201716 | 11/2017 |
| WO | WO2017202014 | 11/2017 |
| WO | WO2017206022 | 12/2017 |
| WO | WO2017206480 | 12/2017 |
| WO | WO2017215221 | 12/2017 |
| WO | WO2018000756 | 1/2018 |
| WO | WO2018000760 | 1/2018 |
| WO | WO2018000761 | 1/2018 |
| WO | WO2018000829 | 1/2018 |
| WO | WO2018001105 | 1/2018 |
| WO | WO2018001106 | 1/2018 |
| WO | WO2018023890 | 2/2018 |
| WO | WO2018040380 | 3/2018 |
| WO | WO2018053955 | 3/2018 |
| WO | WO2018058883 | 4/2018 |
| WO | WO2018058884 | 4/2018 |
| WO | WO2018095312 | 5/2018 |
| WO | 2003035030 A1 | 5/2023 |

OTHER PUBLICATIONS

Yeo & Friend, "Ultrafast microfluidics using surface acoustic waves", American Institute of Physics, vol. 3, Issue 1, 2009, pp. 1-23. Retrieved from the Internet <URL: https://aip.scitation.org/doi/10.1063/1.3056040> <DOI: 10.1063/1.3056040>.

Qi et al., "Miniature inhalation therapy platform using surface acoustic wave microfluidic atomization", The Royal Society of Chemistry, Issue 15, May 2009, pp. 2184-2193. Retrieved from the Internet <URL: https://pubs.rsc.org/en/content/articlelanding/2009/LC/b903575c#!divAbstract> <DOI: 10.1039/b903575c>.

Ariyakul & Nakamoto, "Olfactory Display Using a Miniaturized Pump and a SAW Atomizer for Presenting Low-volatile Scents", IEEE Virtual Reality, Singapore, Mar. 2011, pp. 193-194.

Olszewski et al., "A silicon-based MEMS vibrating mesh nebulizer for inhaled drug delivery", Procedia Engineering, vol. 168, 2016, pp. 1521-1524. Retrieved from the Internet <URL: https://www.sciencedirect.com/science/article/pii/S1877705816337729?via%3Dihub> <DOI: 10.1016/j.proeng.2016.11.451>.

Hawkins & Feng, "Vibrating Mesh Nebulizer Reference Design", Microchip Technology Inc., 2016-2017, pp. 1-50.

International Search Report in the corresponding International Application No. PCT/IB2020/059731, dated Dec. 11, 2020, 5 pages.

\* cited by examiner

AEROSOL DELIVERY DEVICE WITH DUAL RESERVOIR

CROSS-REFERENCE TO RELATED APPLICATIONS

This application is a continuation application of U.S. patent application Ser. No. 17/699,805, filed on Mar. 21, 2022, which is a continuation application of U.S. patent application Ser. No. 16/657,219, filed on Oct. 18, 2019, each of which is incorporated herein in its entirety by reference.

TECHNOLOGICAL FIELD

The present disclosure relates to aerosol delivery devices, and more particularly to an aerosol delivery device that includes one or more reservoirs and one or more atomization assemblies, which may utilize electrical power to vaporize one or more liquid compositions for the production of an aerosol. In various implementations, the liquid compositions, which may incorporate materials and/or components that may be made or derived from tobacco or otherwise incorporate tobacco or other plants, may include natural or synthetic components including flavorants, and/or may include one or more medicinal components, are vaporized by the atomization assemblies to produce an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al., which are incorporated herein by reference in their entireties. See also, for example, the various types of smoking articles, aerosol delivery devices, and electrically powered sources referenced by brand name and commercial source in U.S. Pat. App. Pub. No. 2015/0216232 to Bless et al., which is incorporated herein by reference in its entirety.

However, it would be desirable to provide an aerosol delivery device with enhanced functionality. In this regard, it is desirable to provide an aerosol delivery with advantageous features.

BRIEF SUMMARY

The present disclosure relates to aerosol delivery devices, methods of forming such devices, and elements of such devices. The disclosure particularly relates to an aerosol delivery device. The present disclosure includes, without limitation, the following example implementations:

An aerosol delivery device comprising a housing defining an outer wall, and further including a power source and a control component, a mouthpiece portion that defines an aerosol exit path, a first reservoir configured to contain a first liquid composition, a second reservoir configured to contain a second liquid composition, a first atomization assembly configured to vaporize the first liquid composition to generate a first aerosol having a first aerosol particle size, and a second atomization assembly configured to vaporize the second liquid composition to generate a second aerosol having a second aerosol particle size, wherein the first liquid composition is different than the second liquid composition, and wherein the first particle size is different than the second particle size.

The aerosol delivery device of any preceding example implementation, or any combination of any preceding example implementations, wherein at least one of the first and second atomization assemblies comprises a vibrating assembly.

The aerosol delivery device of any preceding example implementation, or any combination of any preceding example implementations, wherein one of the first and second vibrating assemblies comprises a mesh plate and a vibrating component.

The aerosol delivery device of any preceding example implementation, or any combination of any preceding example implementations, wherein the vibrating component of one of the first and second vibrating assemblies comprises a piezoelectric ring affixed to and substantially surrounding the mesh plate.

The aerosol delivery device of any preceding example implementation, or any combination of any preceding example implementations, wherein the mesh plate of one of the first and second vibrating assemblies is substantially flat.

The aerosol delivery device of any preceding example implementation, or any combination of any preceding example implementations, wherein at least a portion of the mesh plate of at least one of the first and second vibrating assemblies is convex with respect to the respective reservoir.

The aerosol delivery device of any preceding example implementation, or any combination of any preceding example implementations, wherein the first and second reservoirs and the first and second atomization assemblies are contained in the housing, and wherein the mouthpiece portion is configured to be removable and replaceable from the housing.

The aerosol delivery device of any preceding example implementation, or any combination of any preceding example implementations, wherein the first and second reservoirs are located on opposite sides of the aerosol exit path.

The aerosol delivery device of any preceding example implementation, or any combination of any preceding example implementations, wherein the first and second atomization assemblies are located on opposites sides of the aerosol exit path.

The aerosol delivery device of any preceding example implementation, or any combination of any preceding example implementations, wherein the first and second atomization assemblies are angled toward each other and the aerosol exit path.

The aerosol delivery device of any preceding example implementation, or any combination of any preceding example implementations, wherein a surface of each of the first and second atomization assemblies forms an angle with respect to the aerosol exit path.

The aerosol delivery device of any preceding example implementation, or any combination of any preceding example implementations, wherein the angle formed by a surface of each of the first and second atomization assemblies is greater than 45 degrees and less than 180 degrees.

The aerosol delivery device of any preceding example implementation, or any combination of any preceding example implementations, wherein the first particle size is smaller than approximately 4 microns.

The aerosol delivery device of any preceding example implementation, or any combination of any preceding example implementations, wherein the second particle size is larger than approximately 4 microns.

The aerosol delivery device of any preceding example implementation, or any combination of any preceding example implementations, wherein the second particle size between approximately 4 microns and approximately 15 microns.

The aerosol delivery device of any preceding example implementation, or any combination of any preceding example implementations, wherein the first and second atomization assemblies are configured to generate the first and second aerosols substantially simultaneously.

The aerosol delivery device of any preceding example implementation, or any combination of any preceding example implementations, wherein the first atomization assembly is configured generate the first aerosol after the second atomization assembly is configured to generate the second aerosol.

The aerosol delivery device of any preceding example implementation, or any combination of any preceding example implementations, wherein the first and second atomization assemblies are configured to be independently controllable via the control component.

The aerosol delivery device of any preceding example implementation, or any combination of any preceding example implementations, wherein the first liquid composition comprises a water-based liquid that includes nicotine.

The aerosol delivery device of any preceding example implementation, or any combination of any preceding example implementations, wherein the second liquid composition includes a pulmonary surfactant.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWING(S)

In order to assist the understanding of aspects of the disclosure, reference will now be made to the appended drawings, which are not necessarily drawn to scale and in which like reference numerals refer to like elements. The drawings are provided by way of example to assist understanding of aspects of the disclosure, and should not be construed as limiting the disclosure.

DETAILED DESCRIPTION

Figure 1:
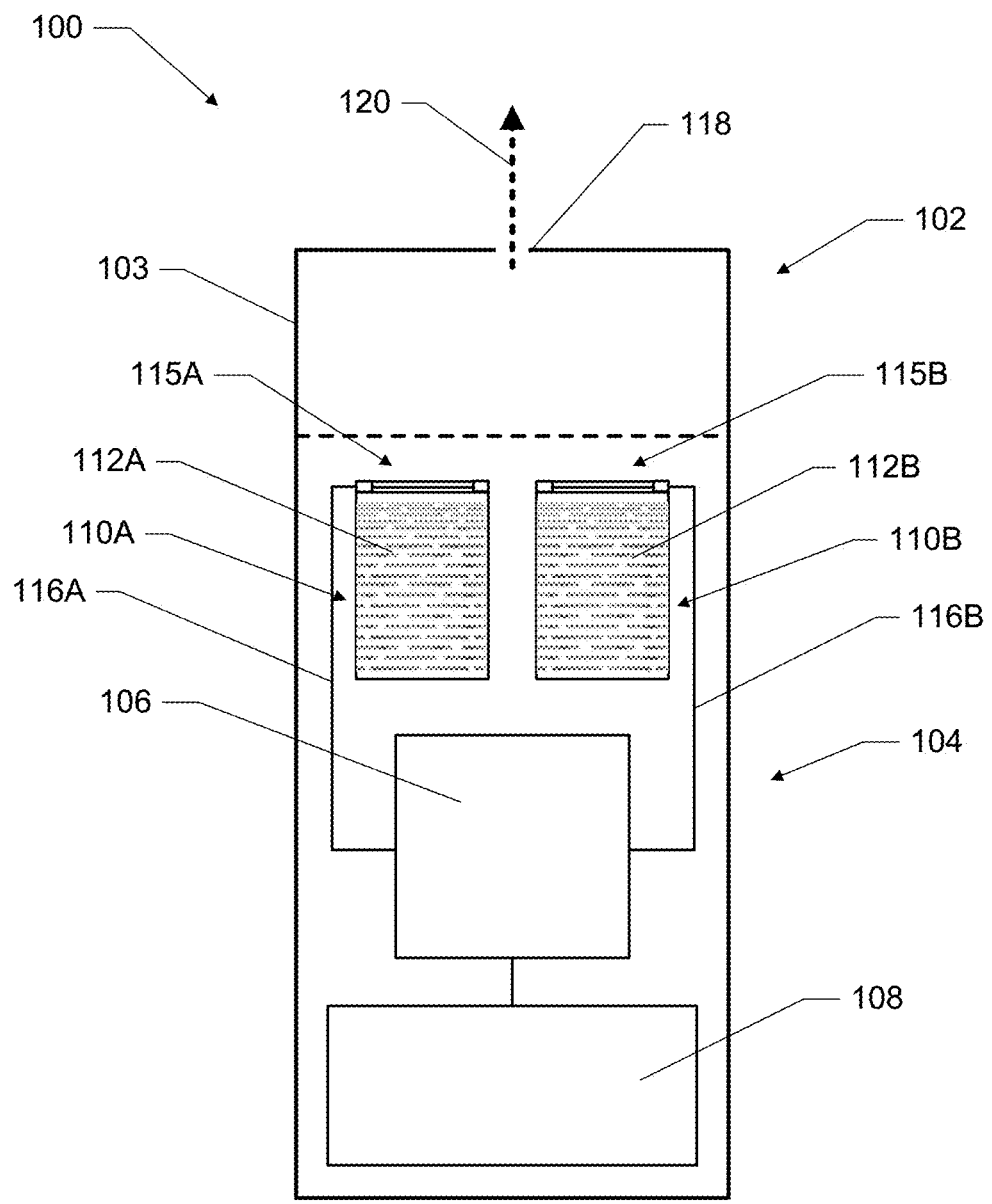
FIG. 1 illustrates a top schematic view of an aerosol delivery device, according to an example implementation of the present disclosure.

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a" "an", "the", include plural referents unless the context clearly dictates otherwise.

As described hereinafter, embodiments of the present disclosure relate to aerosol delivery devices or vaporization devices, said terms being used herein interchangeably. Aerosol delivery devices according to the present disclosure use electrical energy to vaporize a material (preferably without combusting the material to any significant degree and/or without significant chemical alteration of the material) to form an inhalable substance; and components of such devices have the form of articles that most preferably are sufficiently compact to be considered hand-held devices. That is, use of components of some aerosol delivery devices does not result in the production of smoke—i.e., from by-products of combustion or pyrolysis of tobacco, but rather, use of those systems results in the production of vapors resulting from vaporization of an aerosol precursor composition. In some embodiments, components of aerosol delivery devices may be characterized as electronic cigarettes, and those electronic cigarettes most preferably incorporate tobacco and/or components derived from tobacco, and hence deliver tobacco derived components in aerosol form. It will be appreciated, however, that devices in accordance with various embodiments can be used to deliver active ingredients other than nicotine and/or tobacco components. Other examples include delivery devices for botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)).

Aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol delivery device of the present disclosure can hold and use the device much like a smoker employs a traditional type of smoking article, draw on one end of that device for inhalation of aerosol produced by that device, take or draw puffs at selected intervals of time, and the like.

Aerosol delivery devices of the present disclosure may also be characterized as being vapor-producing articles or medicament delivery articles. Thus, such articles or devices may be adapted so as to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), an atomization assembly, a liquid composition (e.g., commonly an aerosol precursor composition liquid capable of yielding an aerosol, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated may be withdrawn therefrom upon draw).

Alignment of the components within the aerosol delivery device may be variable. In specific embodiments, the liquid composition may be located between two opposing ends of the device (e.g., within a reservoir of the device, which in certain circumstances may be replaceable and disposable or refillable). Other configurations, however, are not excluded. Generally, the components are configured relative to one another so that energy from the atomization assembly vaporizes the liquid composition (as well as one or more flavorants, medicaments, or the like that may likewise be provided for delivery to a user) and forms an aerosol for delivery to the user. When the atomization assembly vaporizes the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof.

More specific formats, configurations and arrangements of components within the aerosol delivery devices of the present disclosure will be evident in light of the further disclosure provided hereinafter. Additionally, the selection and arrangement of various aerosol delivery device components may be appreciated upon consideration of the commercially available electronic aerosol delivery devices, such as those representative products referenced in the background art section of the present disclosure.

FIG. 1 illustrates an aerosol delivery device, according to an example implementation of the present disclosure. In particular, FIG. 1 illustrates a schematic view of an aerosol delivery device 100 comprising a mouthpiece portion 102 and a housing 104. In the depicted implementation, the mouthpiece portion 102 may be permanently or detachably aligned in a functioning relationship with the housing 104. In some implementations, for example, the mouthpiece portion and the housing may comprise a single part, whereas in other implementations, a connection therebetween may be releasable such that, for example, the housing and/or the mouthpiece portion may be reused and/or may be disposable and/or refillable. In other implementations, the mouthpiece portion may not be linearly aligned with the housing, such as implementations in which the mouthpiece portion and the housing are in a side-by-side arrangement. In various implementations, a variety of different means of engagement may be used to couple a mouthpiece portion and a housing together. For example, in some implementations the mouthpiece portion and the housing may be coupled via one or more of a snap-fit engagement, a press-fit engagement, an interference engagement, a threaded engagement, a bayonet connection, a magnetic engagement, etc. In some implementations, the housing may include a chamber configured to receive at least a portion of the mouthpiece portion. In other implementations, the mouthpiece portion may include a chamber configured to receive at least a portion of the housing. In some implementations, an electrical connection may be created between the mouthpiece portion and the housing. In some implementations, such an electrical connection may exist via one or more components of the coupling features. In such a manner, corresponding electrical contacts in the mouthpiece portion and the housing may be substantially aligned after coupling to provide the electrical connection. It should be noted that the components depicted in this and the other figures are representative of the components that may be present in a housing and/or mouthpiece portion and are not intended to limit the scope of the housing and/or mouthpiece portion components that are encompassed by the present disclosure. Some examples of mechanical and electrical connections between components of aerosol delivery devices are described in U.S. patent application Ser. No. 16/386,940, filed on Apr. 17, 2019, and titled Connectors for Forming Electrical and Mechanical Connections Between Interchangeable Units in an Aerosol Delivery System, the disclosure of which is incorporated herein by reference in its entirety. Other connectors are described in U.S. Pat. App. Pub. No. 2014/0261495 to Novak et al., the disclosure of which is incorporated herein by reference in its entirety.

In various implementations, the aerosol delivery device may have a variety of different shapes. For example, in some implementations the aerosol delivery device may be substantially rod-like or substantially tubular shaped or substantially cylindrically shaped. In other implementations, however, other shapes and dimensions are possible (e.g., rectangular, oval, hexagonal, prismatic, regular or irregular polygon shapes, disc-shaped, cube-shaped, multifaceted shapes, or the like). It should be noted for purposes of the present disclosure that the term "substantially" should be understood to mean approximately and/or within a certain degree of manufacturing tolerance as would be understood by one skilled in the art.

In specific implementations, one or both of the housing or the mouthpiece portion may be referred to as being disposable or as being reusable. For example, in some implementations the housing may include a power source. In some implementations, the power source may comprise a replaceable battery or a rechargeable battery and thus may be combined with any type of recharging technology, including connection to a wall charger, connection to a car charger (e.g., cigarette lighter receptacle, USB port, etc.), connection to a computer, any of which may include a universal serial bus (USB) cable or connector (e.g., USB 2.0, 3.0, 3.1, USB Type-C), connection to a USB connector (e.g., USB 2.0, 3.0, 3.1, USB Type-C as may be implemented in a wall outlet, electronic device, vehicle, etc.), connection to a photovoltaic cell (sometimes referred to as a solar cell) or solar panel of solar cells, or wireless charger, such as a charger that uses inductive wireless charging (including for example, wireless charging according to the Qi wireless charging standard from the Wireless Power Consortium (WPC)), or a wireless radio frequency (RF) based charger, and connection to an array of external cell(s) such as a power bank to charge a device via a USB connector or a wireless charger. An example of an inductive wireless charging system is described in U.S. Pat. App. Pub. No. 2017/0112196 to Sur et al., which is incorporated herein by reference in its entirety. In some implementations, the power source may comprise a photovoltaic system. In further implementations, a power source may also comprise a capacitor. Capacitors are capable of discharging more quickly than batteries and can be charged between puffs, allowing a battery to discharge into a capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor. Examples of power supplies that include supercapacitors are described in U.S. Pat. App. Pub. No. 2017/0112191 to Sur et al., which is incorporated herein by reference in its entirety.

Referring back to FIG. 1, the housing 104 of the depicted implementation includes a control component 106 (e.g., a printed circuit board (PCB), an integrated circuit, a memory component, a microcontroller, or the like), and a power source, such as a battery 108. Additional components may also be included, such as, for example, one or more sensors (e.g., one or more flow sensors), one or more indicators (e.g., one or more light-emitting diodes (LEDs)), one or more input elements (e.g., one or more buttons), etc. Some example types of electronic components, structures, and configurations thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. App. Pub. Nos. 2009/0230117 to Fernando et al., 2014/0060554 to Collet et al., and 2014/0270727 to Ampolini et al.; and U.S. Pat. App. Pub. No. 2015/0257445 to Henry et al.; which are incorporated herein by reference in their entireties. Some examples of batteries that may be applicable to the present disclosure are described in U.S. Pat. App. Pub. No. 2010/0028766 to Peckerar et al., the disclosure of which is incorporated herein by reference in its entirety. In some implementations, further indicators (e.g., a haptic feedback component, an audio feedback component, or the like) may be included in addition to or as an alternative to an LED. Additional representative types of components that yield visual cues or indicators, such as LED components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. App. Pub. No. 2015/0020825 to Galloway et al.; and U.S. Pat. App. Pub. No. 2015/0216233 to Sears et al.; which are incorporated herein by reference in their entireties. It should be understood that in various implementations not all of the illustrated elements may be required. For example, in some implementations an LED may be absent or may be replaced with a different indicator, such as a vibrating indicator. Likewise, a flow sensor may be replaced with a manual actuator, such as, for example, one or more manually actuated push buttons.

In the depicted implementation, the housing 104 also includes a first liquid reservoir 110A, which is configured to contain a first liquid composition 112A, and a second liquid reservoir 110B, which is configured to contain a second liquid composition 112B. In some implementations, the first and second liquid reservoirs may be part of the housing (such as, for example, comprising a molded feature of the housing), while in other implementations, one or both of the first or second liquid reservoirs may comprise a separate part. In some implementations, the first and second reservoirs may comprise one or more refillable liquid reservoirs. As such, in some implementations, one or both of the first or second liquid reservoirs may be reusable. In other implementations, however, one or both of the first or second liquid reservoirs may be disposable. In some implementations, at least one of the liquid reservoirs may comprise an independent container (e.g., formed of walls substantially impermeable to the liquid composition). In some implementations, the walls of at least one of the liquid reservoirs may be flexible and/or collapsible, while in other implementations the walls of at least one of the liquid reservoirs may be substantially rigid. Some examples of types of substrates, reservoirs, or other components for supporting a liquid composition are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety.

In some implementations, the housing and/or the mouthpiece portion may be made of a polymeric material that, in further implementations, may be at least partially transparent or translucent. In some implementations, such materials, may include, but need not be limited to, polycarbonate, acrylic, polyethylene terephthalate (PET), amorphous copolyester (PETG), polyvinyl chloride (PVC), liquid silicone rubber (LSR), cyclic olefin copolymers, polyethylene (PE), ionomer resin, polypropylene (PP), fluorinated ethylene propylene (FEP), styrene methyl methacrylate (SMMA), styrene acrylonitrile resin (SAN), polystyrene, acrylonitrile butadiene styrene (ABS), and combinations thereof. Other materials may include, for example, biodegradable polymers such as, but not limited to, polylactic acid (PLA), polyhydroxyalkanoates (PHA's), and polybutylene succinate (PBS). In some implementations, the housing and/or the mouthpiece portion may be made of a metal or composite material. In some implementations, the housing and/or the mouthpiece portion may be made of other material that may be at least partially transparent or translucent. Such materials may include, for example, glass or ceramic materials.

In various implementations, one or both of the first or second liquid compositions may comprise an aerosol precursor composition. In some implementations, the aerosol precursor composition may incorporate tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. App. Pub. No. 2015/0335070 to Sears et al., the disclosure of which is incorporated herein by reference in its entirety. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine, USP/EP nicotine, etc.). In other implementations, non-tobacco materials alone may form the aerosol precursor composition. In some implementations, the aerosol precursor composition may include tobacco-extracted nicotine with tobacco or non-tobacco flavors and/or non-tobacco-extracted nicotine with tobacco or non-tobacco flavors.

In some implementations, one or both the first or second liquid compositions, sometimes also referred to as an aerosol precursor composition or a vapor precursor composition or "e-liquid", may comprise a variety of components, which may include, by way of example, water, a polyhydric alcohol (e.g., glycerin, propylene glycol, or a mixture thereof), nicotine, tobacco, tobacco extract, and/or flavorants. Some examples of types of aerosol precursor components and formulations are also set forth and characterized in U.S. Pat. No. 7,217,320 to Robinson et al. and U.S. Pat. App. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

In some implementations, the amount of aerosol precursor that is incorporated within the aerosol delivery system is such that the aerosol generating device provides acceptable sensory and desirable performance characteristics. For example, sufficient amounts of aerosol forming material (e.g., water, glycerin, and/or propylene glycol) may be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating device. In one or more embodiments, about 1 ml or more, about 2 ml or more, about 5 ml or more, or about 10 ml or more of the aerosol precursor composition may be included.

In some of the examples described above, the aerosol precursor composition comprises a glycerol-based liquid. In other implementations, however, the aerosol precursor composition may be a water-based liquid. In some implementations, the water-based liquid may be comprised of more than approximately 80% water. For example, in some implementations the percentage of water in the water-based liquid may be in the inclusive range of approximately 90% to approximately 93%. In some implementations, the water-based liquid may include up to approximately 10% propylene glycol. For example, in some implementations the percentage of propylene glycol in the water-based liquid may be in the inclusive range of approximately 4% to approximately 5%. In some implementations, the water-based liquid may include up to approximately 10% flavorant. For example, in some implementations the percentage of flavorant(s) of the water-based liquid may be in the inclusive range of approximately 3% to approximately 7%. In some implementations, the water-based liquid may include up to approximately 3% nicotine. For example, in some implementations the percentage nicotine in the water-based liquid may be in the inclusive range of approximately 0.1% to approximately 0.3%. In some implementations, the water-based liquid may include up to approximately 10% cyclodextrin. For example, in some implementations the percentage cyclodextrin in the water-based liquid may be in the inclusive range of approximately 3% to 5%. In still other implementations, the aerosol precursor composition may be a combination of a glycerol-based liquid and a water-based liquid. For example, some implementations may include up to approximately 50% water and less than approximately 20% glycerol. The remaining components may include one or more of propylene glycol, flavorants, nicotine, cyclodextrin, etc. Some examples of water-based liquid compositions that may be suitable are disclosed in GB 1817863.2, filed Nov. 1, 2018, titled Aerosolisable Formulation; GB 1817864.0, filed Nov. 1, 2018, titled Aerosolisable Formulation; GB 1817867.3, filed Nov. 1, 2018, titled Aerosolisable Formulation; GB 1817865.7, filed Nov. 1, 2018, titled Aerosolisable Formulation; GB 1817859.0, filed Nov. 1, 2018, titled Aerosolisable Formulation; GB 1817866.5, filed Nov. 1, 2018, titled Aerosolisable Formulation; GB 1817861.6, filed Nov. 1, 2018, titled Gel and Crystalline Powder; GB 1817862.4, filed Nov. 1, 2018, titled Aerosolisable Formulation; GB 1817868.1, filed Nov. 1, 2018, titled Aerosolised Formulation; and GB 1817860.8, filed Nov. 1, 2018, titled Aerosolised Formulation, each of which is incorporated by reference herein in its entirety.

In some implementations, the aerosol precursor composition may incorporate nicotine, which may be present in various concentrations. The source of nicotine may vary, and the nicotine incorporated in the aerosol precursor composition may derive from a single source or a combination of two or more sources. For example, in some implementations the aerosol precursor composition may include nicotine derived from tobacco. In other implementations, the aerosol precursor composition may include nicotine derived from other organic plant sources, such as, for example, non-tobacco plant sources including plants in the Solanaceae family. In other implementations, the aerosol precursor composition may include synthetic nicotine. In some implementations, nicotine incorporated in the aerosol precursor composition may be derived from non-tobacco plant sources, such as other members of the Solanaceae family. The aerosol precursor composition may additionally or alternatively include other active ingredients including, but not limited to, botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)).

As noted above, in various implementations, one or both of the first or second liquid compositions may include a flavorant. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime and lemon, mango, and other citrus flavors), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, amaretto, mojito, yerba santa, ginseng, chamomile, turmeric, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Other examples include flavorants derived from, or simulating, burley, oriental tobacco, flue cured tobacco, etc. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

Referring back to FIG. 1, the first liquid composition 112A of the depicted implementation is in fluid communication (either directly or through one or more additional components) with at least a portion of a first atomization assembly 115A. Likewise, the second liquid composition 112B of the depicted implementation is in fluid communication (either directly or through one or more additional components) with at least a portion of a second atomization assembly 115B. Although in other implementations the first and second atomization assemblies may have a variety of different configurations, in the depicted implementation the first and second atomization assemblies 115A, 115B have an overall substantially planar shape or a domed shape, with each atomization assembly 115A, 115B including a surface that forms a substantially right angle with respect to an aerosol exit path 120. In various implementations, the atomization assemblies may be fluidly coupled with respective portions of the liquid compositions such that the atomization assemblies generate an aerosol from the respective liquid compositions. In the depicted implementation, one or more electrical connections 116A, 116B connect the atomization assemblies 115A, 115B to the control component 106 and/or the battery 108. In such a manner, the atomization assemblies 115A, 115B of the depicted implementation may be energized by the battery 108 and/or control component 106 (e.g., so as to vibrate a component of the atomization assembly at a relatively high rate). Some examples of electronic/control components that may be applicable to the present disclosure are described in U.S. Pat. App. Pub. No. 2019/0014819 to Sur, which is incorporated herein by reference in its entirety.

As noted, in some implementations fluid communication between a liquid composition and a respective atomization assembly may be direct. In other implementations, however, fluid communication between a liquid composition and a respective atomization assembly may be indirect. In various implementations, indirect fluid communication may occur, for example, by transporting (e.g., via a liquid transport element) and/or by depositing (e.g., via a micropump or spray device) liquid composition to a portion of the atomization assembly. In some implementations, at least one of the liquid reservoirs may be substantially sealed to prevent passage of the liquid composition therefrom except via any specific openings or conduits provided expressly for passage of the liquid composition, such as through one or more transport elements as otherwise described herein.

In various implementations, a liquid transport element may have one layer, or multiple layers, and may be made of a single material or multiple materials. In various implementations, the liquid transport element may be any shape and may be a porous, semi-porous, or non-porous absorbent/adsorbent material. In other implementations, there may be a second liquid transport element located between the first liquid transport element and the liquid reservoir, the second liquid transport element being configured to transfer liquid from the liquid reservoir to the first liquid transport element. In such a manner, the first liquid transport element may not be in direct contact with the liquid in the liquid reservoir. In various implementations, the second liquid transport element may be made of the same material or a different material than the first liquid transport element and may have a shape that is the same or differs from that of the first liquid transport element. For example, in some implementations the liquid transport element may be made of fibrous materials (e.g., organic cotton, cellulose acetate, regenerated cellulose fabrics, glass fibers), polymers, silk, particles, porous ceramics (e.g., alumina, silica, zirconia, SiC, SiN, AlN, etc.), porous metals, porous carbon, graphite, porous glass, sintered glass beads, sintered ceramic beads, capillary tubes, porous polymers, or the like. In some implementations, the liquid transport element may be any material that contains an open pore network (i.e., a plurality of pores that are interconnected so that fluid may flow from one pore to another in a plurality of direction through the element). The pores can be nanopores, micropores, macropores or combinations thereof. As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. In some embodiments, the liquid transport element may be a substantially solid non-porous material, such as a polymer or dense ceramic or metals, configured to channel liquid through apertures or slots while not necessarily relying upon wicking through capillary action. Such a solid body may be used in combination with a porous absorptive pad. The absorptive pad may be formed of silica-based fibers, organic cotton, rayon fibers, cellulose acetate, regenerated cellulose fabrics, highly porous ceramic or metal mesh, etc. Some representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, the liquid transport element may be formed partially or completely from a porous monolith, such as a porous ceramic, a porous glass, or the like. Example monolithic materials that may be suitable for use according to embodiments of the present disclosure are described, for example, in U.S. Pat. App. Pub. No. 2017/0188626 to Davis et al., and U.S. Pat. App. Pub. No. 2014/0123989 to LaMothe, the disclosures of which are incorporated herein by reference in their entireties. In some implementations, the porous monolith may form a substantially solid wick.

In some implementations, an end of a liquid transport element may be configured to be placed proximate an atomization assembly and a liquid composition in a reservoir so that the liquid transport element acts as a secondary reservoir that absorbs or adsorbs the liquid from the reservoir so that the mesh plate is in contact with the liquid composition, even if there is no longer liquid in the reservoir. In such a manner, the liquid transport element is configured to facilitate delivery of the liquid composition to the atomization assembly.

In some implementations, the liquid composition may be driven through a component of the atomization assembly resulting in the generation of a plurality of aerosol particles. Likewise, in other implementations, vibration of a component of the atomization assembly may create ultrasonic waves within the liquid composition and/or surface acoustic waves in the liquid composition, that result in the formation of an aerosol at the surface of the liquid composition. In some implementations the liquid composition may be applied and/or transferred to a component of the atomization assembly to create the aerosol.

In various implementations, the housing and/or the mouthpiece portion may include one or more air intakes (not shown), which may comprise one or more openings allowing for passage of ambient air into the housing and/or mouthpiece portion. In some implementations, the air intake may draw air into and/or around one or more of the atomization assemblies, where it may be mixed with the vaporized liquid composition to comprise the aerosol that is delivered to the user. It should be noted that in some implementations the air intake need not be adjacent the housing, and, in some implementations, may be located downstream from one or more of the atomization assemblies. As noted, in some implementations, one or more air intakes may be formed through the mouthpiece portion (e.g., such that it does not enter the housing) or some other portion of the aerosol delivery device. It should be noted that some implementations need not include a mouthpiece portion and/or the mouthpiece portion may be integral with the housing.

In various implementations, the mouthpiece portion may also include at least one electronic component, which may include an integrated circuit, a memory component, a sensor, or the like, although such a component need not be included. In some implementations that include such a component, the electronic component may be adapted to communicate with the control component of the housing and/or with an external device by wired or wireless means. In various implementations, an electronic component of the mouthpiece portion may be positioned anywhere within the mouthpiece portion.

In some implementations, the aerosol delivery device may include at least one flow sensor that may comprise a different component than the control component. In other implementations, the control component and the flow sensor may be combined as an electronic circuit board with the air flow sensor attached directly thereto. Some examples of air flow sensors that may be applicable to the present disclosure are described in U.S. patent application Ser. No. 16/260,901, filed on Jan. 29, 2019, to Sur, the disclosure of which is incorporated herein by reference in its entirety. In some implementations, the air flow sensor may comprise its own circuit board or other base element to which it can be attached. In some embodiments, a flexible circuit board may be utilized. A flexible circuit board may be configured into a variety of shapes, include substantially tubular shapes. Configurations of a printed circuit board and a pressure sensor, for example, are described in U.S. Pat. App. Pub. No. 2015/0245658 to Worm et al., the disclosure of which is incorporated herein by reference in its entirety. Additional types of sensing or detection mechanisms, structures, and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In some implementations, when a user draws on the device, airflow may be detected by a sensor, and one or both of the atomization assemblies 115A, 115B may be activated to vaporize the respective liquid compositions. As noted above, in some implementations drawing upon the mouthend of the device causes ambient air to enter the device. The drawn air may then combine with the formed vapor to form the aerosol. The aerosol may then be whisked, aspirated, or otherwise drawn away from the atomization assemblies and out of an opening 118 in the mouthend of the device, along the aerosol exit path 120. In other implementations, in the absence of an airflow sensor, one or both of the atomization assemblies may be activated manually, such as via one or more push buttons (not shown). Additionally, in some implementations, the air intake may occur through the mouthpiece portion, and/or through the housing, and/or between the mouthpiece portion and the housing. It should be noted that in some implementations, there may be one or more components between one or both of the atomization assemblies and the opening in the mouthend of the device. For example, in some implementations one or more heating components may be located downstream from either or both of the atomization assemblies. In various implementations, a heating component may comprise any device having any shape and/or configuration that is configured to elevate the temperature of the generated aerosol, including, for example, one or more coil heating components, ceramic heating components, etc.

In some implementations, one or more input elements may be included with the aerosol delivery device (and may replace or supplement an airflow sensor, pressure sensor, or manual push button). In various implementations, an input element may be included to allow a user to control functions of the device and/or for output of information to a user. Any component or combination of components may be utilized as an input for controlling the function of the device. For example, one or more pushbuttons may be used as described in U.S. Pat. App. Pub. No. 2015/0245658 to Worm et al., which is incorporated herein by reference in its entirety. Likewise, a touchscreen may be used as described in U.S. Pat. App. Pub. No. 2016/0262454 to Sears et al., which is incorporated herein by reference in its entirety. As a further example, components adapted for gesture recognition based on specified movements of the aerosol delivery device may be used as an input. See U.S. App. Pub. No. 2016/0158782 to Henry et al., which is incorporated herein by reference in its entirety. As still a further example, a capacitive sensor may be implemented on the aerosol delivery device to enable a user to provide input, such as by touching a surface of the device on which the capacitive sensor is implemented.

In some embodiments, an input element may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pat. App. Pub. No. 2016/0007561 to Ampolini et al., the disclosure of which is incorporated herein by reference in its entirety. In such implementations, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

Yet other features, controls or components that may be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference in their entireties.

In various implementations, one or both of the atomization assemblies may comprise a variety of different components or devices configured to generate an aerosol from the liquid composition. For example, in some implementations the atomization assembly may comprise a jet nebulizer assembly, which may be configured to utilize compressed air to generate an aerosol. In other implementations, the atomization assembly may comprise an ultrasonic assembly, which may be configured to utilize the formation of ultrasonic waves within the liquid composition to generate an aerosol. In other implementations, the atomization assembly may comprise a vibrating mesh assembly, which may comprise a piezoelectric material (e.g., a piezoelectric ceramic material) affixed to and substantially surrounding a mesh plate, (e.g., a perforated plate such as a micro-perforated mesh plate) that is vibrated within the liquid composition or proximate the surface of the liquid composition to generate an aerosol. In still other implementations, the atomization assembly may comprise a surface acoustic wave (SAW) or Raleigh wave assembly, which may utilize surface wave characteristics to generate an aerosol at the surface of the liquid composition. It should be noted that for purpose of this application, an ultrasonic assembly may be any assembly configured to create ultrasonic waves within the liquid composition. In some implementations, for example, a vibrating mesh assembly may also operate as an ultrasonic assembly.

Referring back to FIG. 1, in the depicted implementation the first reservoir 110A contains a first liquid composition 112A, and the second reservoir 110B contains a second liquid composition 112B. Although in various implementations the first and second liquid compositions may comprise any of the liquid compositions or any combination of the liquid compositions described above, in the depicted implementation the first and second reservoirs 110A, 110B contain respective first and second liquid compositions 112A, 112B that are different from each other. In addition, although in some implementations the atomization assemblies may generate aerosols having substantially the same particle size, in the depicted implementation the first and second atomization assemblies 115A, 115B are configured to generate respective aerosols having particle sizes that are different from each other. In particular, in the depicted implementation the first liquid composition 112A comprises an unflavored water-based liquid composition that includes water and nicotine and may further include lower concentrations of other components, including, for example, propylene glycol, vegetable glycerin, ethyl alcohol, etc. The first atomization assembly 115A of the depicted implementation comprises a first vibrating assembly that is configured to generate aerosol particles smaller than approximately 4 microns. In the depicted implementation, the second liquid composition 112B comprises a liquid composition that includes a pulmonary surfactant including, but not limited to, various phospholipids, dipalmitoylphosphatidylchlorine (DPPC), surfactant proteins (SP-A, SP-B, SP-C, SP-D, etc.), neutral lipids (cholesterol) and may further include lower concentrations of other components, including, for example, water, ethyl alcohol, propylene glycol, vegetable glycerin, etc. In some implementations, surfactant-soluble flavor packages may be added to this liquid. In some implementations, the viscosity and other properties of the liquid composition may be controlled and adjusted by adding other compatible solvents. The second atomization assembly 115B of the depicted implementation comprises a second vibrating assembly that is configured to generate aerosol particles larger than 4 microns. For example, in some implementations, the second vibrating assembly may be configured to generate aerosol particles between approximately 4 microns and approximately 10 microns. In some implementations, the second vibrating assembly may be configured to generate aerosol particles between approximately 4 microns and approximately 15 microns.

Figure 2:
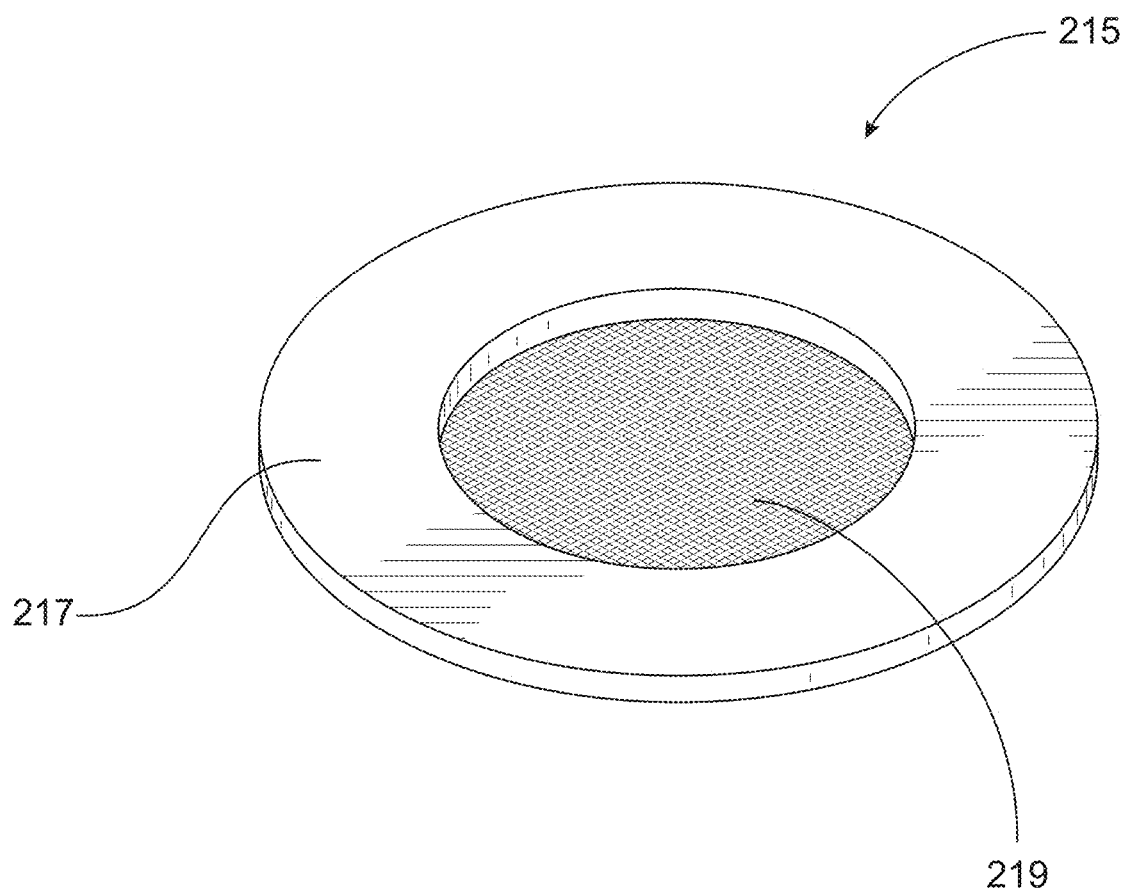
FIG. 2 illustrates a perspective view of a portion of an atomization assembly, according to an example implementation of the present disclosure.

An example of an atomization assembly, which in some implementations may represent one or both of the atomization assemblies of the implementation depicted in FIG. 1, is shown in FIG. 2. In particular, FIG. 2 illustrates an atomization assembly 215 that comprises a vibrating component 217 and a mesh plate 219. In other implementations, additional components may be included. For example, in some implementations a supporting component may be included that is located on the side of the mesh plate opposite the vibrating component (e.g., such that the mesh plate is sandwiched between the supporting component and the vibrating component). Although other configurations are possible, in some implementations, the supporting component may comprise a supporting ring. In various implementations, the supporting component may be made of any suitable material, including, but not limited to, polymeric, metal, and/or ceramic materials. In such a manner, in some implementations the supporting component may increase the longevity of the mesh plate. In some implementations, the supporting component may be replaceable, while in other implementations the supporting component may be affixed to the mesh plate and/or the vibrating component. In some implementations, an auxiliary component may be used that is located between mesh plate and the vibrating component. Although other configurations are possible, in some implementations, the auxiliary component may comprise an auxiliary ring. In various implementations, the auxiliary component may be made of any suitable material, including, but not limited to, polymeric, metal, and/or ceramic materials. In such a manner, the auxiliary component may facilitate the interfacial contact of the components. In some implementations, the auxiliary component may be replaceable, while in other implementations the auxiliary component may be affixed to the mesh plate and/or the vibrating component.

In some implementations, the vibrating component and the mesh plate may be permanently affixed to each other such as, for example, by affixing the components together via an adhesive, such as, for example, an epoxy or other glue, or by ultrasonic welding, mechanical fasteners, etc., while in other implementations, the vibrating component and the mesh plate may not permanently affixed to each other. Rather, they may be separable and held or forced into contact with each other. In various implementations, the mesh plate may have a variety of different configurations. For example, in some implementations the mesh plate may have a substantially flat profile. In other implementations, the mesh plate may have a substantially domed shape, which may be concave or convex with respect to the reservoir and/or the liquid composition. In other implementations, the mesh plate may include a substantially flat portion and a domed portion. In various implementations, the mesh plate may be made of a variety of different materials. In some implementations, the mesh plate may be made of a metal material, such as, but not limited to, stainless steel, palladium-nickel, or titanium. In other implementations, the mesh plate may be made of a polymeric material, such as, for example, a polyimide polymer. In still other implementations, the mesh plate may be made of a combination of materials.

Figure 3A:
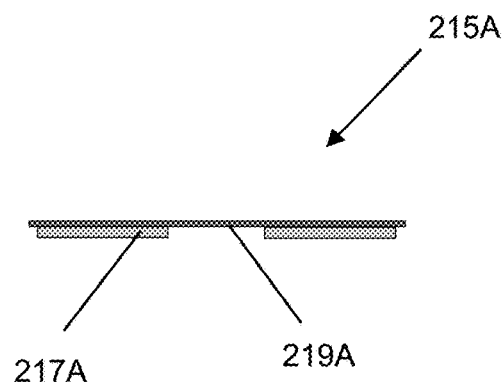
FIG. 3A illustrates a side schematic view of a portion of an atomization assembly, according to an example implementation of the present disclosure.
Figure 3B:
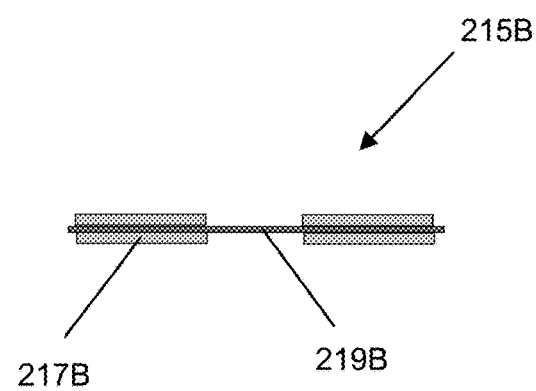
FIG. 3B illustrates a side schematic view of a portion of an atomization assembly, according to an example implementation of the present disclosure.
Figure 3C:
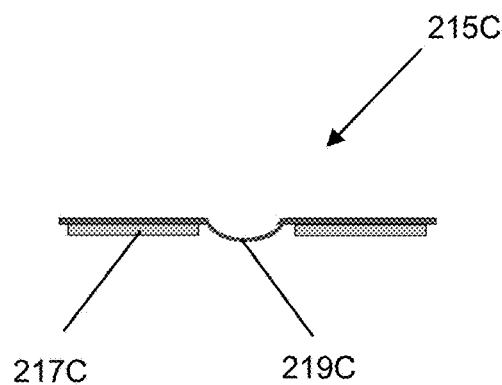
FIG. 3C illustrates a side schematic view of a portion of an atomization assembly, according to an example implementation of the present disclosure.
Figure 3D:
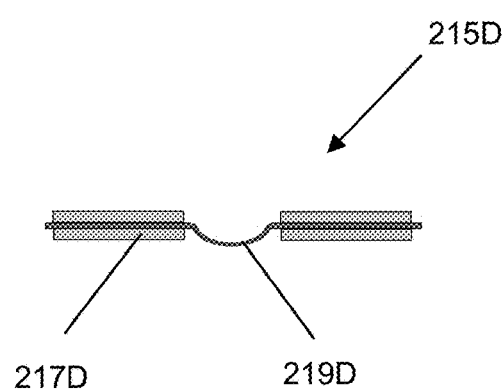
FIG. 3D illustrates a side schematic view of a portion of an atomization assembly, according to an example implementation of the present disclosure.
Figure 3E:
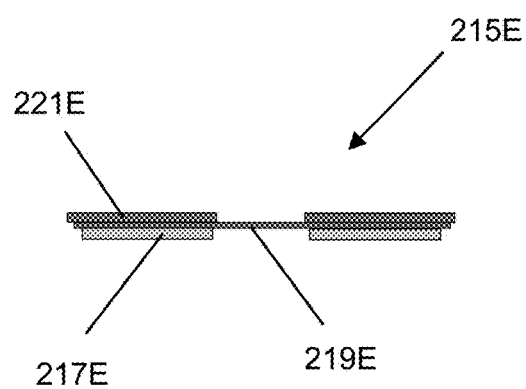
FIG. 3E illustrates a side schematic view of a portion of an atomization assembly, according to an example implementation of the present disclosure.
Figure 3F:
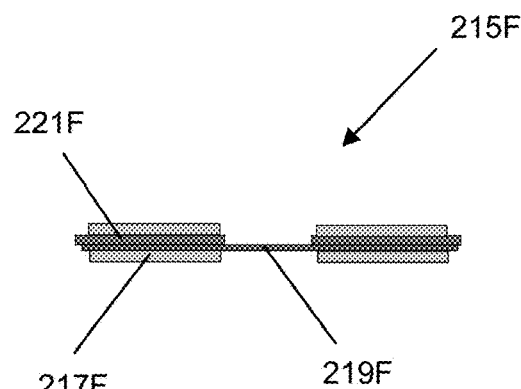
FIG. 3F illustrates a side schematic view of a portion of an atomization assembly, according to an example implementation of the present disclosure.

In various implementations, the structure of one or both of the first or second atomization assemblies may vary. For example, FIGS. 3A-3F illustrate example implementations of various atomization assemblies. In some implementations, one or both of the first or second atomization assemblies of the implementation depicted in FIG. 1 may have one of these configurations. It should be noted that in some implementations, both of the first and second atomization assemblies may have the same configuration, while in other implementations the first and second atomization assemblies may have different configurations. In particular, FIG. 3A illustrates an atomization assembly comprising a piezoelectric ring 217A affixed to and substantially surrounding a mesh plate 219A. FIG. 3B illustrates an atomization assembly comprising a mesh plate 219B sandwiched between two portions of piezoelectric ring 217B. FIG. 3C illustrates an atomization assembly comprising a piezoelectric ring 217C affixed to and substantially surrounding a mesh plate 219C, wherein at least a portion of the mesh plate 219C is curved. FIG. 3D illustrates an atomization assembly comprising a mesh plate 219D sandwiched between two portions of a piezoelectric ring 217D, wherein at least a portion of the mesh plate 219D is curved. FIG. 3E illustrates an atomization assembly comprising a piezoelectric ring 217E affixed to and substantially surrounding one side of a mesh plate 219E, wherein the other side of the mesh plate 219E includes a metal ring 221E substantially surrounding and affixed thereto. FIG. 3F illustrates an atomization assembly comprising a mesh plate 219F one side of which includes a metal ring 221F substantially surrounding and affixed thereto, the mesh plate 219F and metal ring 221F sandwiched between two portions of a piezoelectric ring 217F. It should be noted that in other implementations one or both of the atomization assemblies of the present invention need not be limited to these configurations.

Referring back to FIG. 2, the mesh plate 219 of the depicted implementation includes a plurality of perforations. In some implementations, the perforations may be defined by circular openings in the surfaces of the plate. In other implementations, the perforations may be defined by non-circular openings in the surfaces of the plate, such as, for example, oval, rectangular, triangular, or regular or irregular polygon openings. In various implementations, the perforations may be created using a variety of different methods, including, but not limited to, via a laser (e.g., a femtosecond laser) or via electroplating (e.g., lithography or focused ion beams) or via use of high or low energy focused ion or electron beams. In various implementations, the shapes defined through the plate by the perforations may vary. For example, in some implementations the shapes defined through the plate by the perforations may be substantially cylindrical. In other implementations, the shapes defined through the plate by the perforations may be substantially conical (e.g., having a truncated conical shape defining smaller openings on one surface of the plate and larger openings on the opposite surface of the plate). In other implementations, the shapes defined through the plate by the perforations may be tetragonal or pyramidal. It is believed that in some implementations, substantially conical perforations may increase the performance of the mesh in atomizing the liquid composition. Although any orientation of the mesh plate may be used, in some implementations with perforations defining substantially conical shapes through the plate, the larger openings may be located proximate the surface of the liquid composition and the smaller openings may define an aerosol outlet area. In some implementations with perforations having a substantially conical shapes, the smaller openings may have a size in the inclusive range of approximately 1 micron up to approximately 10 microns, with an average size of approximately 2 microns to approximately 5 microns. In other implementations, the smaller openings may have a size in the inclusive range of approximately several hundred nanometers up to approximately 4 microns, with an average size of approximately 2 microns to approximately 3.1 microns. In other implementations, the smaller end may have a size in the inclusive range of approximately several hundred nanometers to approximately 2 microns, with an average size of approximately 1 micron. In some implementations, the larger openings may have a size in the inclusive range of approximately 10 microns to approximately 60 microns, with an average size of approximately 20 microns to approximately 30 microns. In other implementations, the larger openings may have a size in the inclusive range of approximately 5 microns to approximately 20 microns, with an average size of approximately 10 microns. In some implementations, the size of the perforations may be substantially uniform throughout the perforated portion of the plate; however, in other implementations, the size of the perforations may vary. In such a manner, the formed aerosol may have different size aerosol droplets. For example, in some implementations the perforations may be larger in one portion of the plate and smaller in another portion of the plate. Such portions may include, for example, the center of the plate and a periphery of the plate, or alternating rings that extend radially from the center of the plate.

In various implementations, the mesh plate may have any number of perforations. In some implementations, for example, a number of perforations in the mesh plate may be in the inclusive range of approximately 200 to approximately 6,000, with an average number of perforations of approximately 1,100 to approximately 2,500. In other implementations, a number of perforations in the mesh plate may be in the inclusive range of approximately 400 to approximately 1,000. In various implementations, the thickness of the vibrating component and the thickness of the mesh plate may vary. For example, in some implementations the thickness of the mesh plate may be in the range of a few microns to a few millimeters. In various implementations, the overall diameter of a mesh plate may vary. For example, in some implementations the overall diameter of the mesh plate may be in the inclusive range of approximately a few millimeters to approximately 30 millimeters. In some implementations, the outer diameter of the vibrating component may be larger than the overall diameter of the mesh plate. In other implementations, the outer diameter of the vibrating component may be substantially the same size as the overall diameter of the mesh plate. In still other implementations, the outer diameter of the vibrating component may be smaller than the overall diameter of the mesh plate. In various implementations, the diameter of the perforation area may be smaller than the overall diameter of the mesh plate. For example, in some implementations the diameter of the perforated area may be in the inclusive range of approximately 1 millimeter to approximately 20 millimeters, with an average of approximately 4 millimeters to approximately 12 millimeters. In some implementations, the inner diameter of the vibrating component may be larger than the diameter of the perforated area of the mesh plate. In other implementations, the inner diameter of the vibrating component may be substantially the same as, or smaller than, the diameter of the perforated area of the mesh plate. In some implementations, the thickness of the vibrating component may be in the inclusive range of a few hundred microns to tens of millimeters. For example, in some implementations the thickness of the vibrating component may be smaller than 1 millimeter.

In various implementations, the vibrating component may comprise a piezoelectric component. For example, in various implementations the vibrating component may comprise a piezoelectric ring, which, in some implementations may be made of a piezoceramic material. It should be noted that while the depicted implementation describes a piezoelectric component in the form of a piezoelectric ring, in other implementations the piezoelectric component need not be limited to a ring-shaped object. For example, in some implementations the piezoelectric component may have rectangular, oval, hexagonal, triangular, and regular or irregular polygon shapes. In general, piezoceramic materials possess piezoelectric properties (e.g., ferroelectric properties), wherein they are configured to change shape to a small extent (e.g., 1-2 microns in our application) when exposed to an electrical stimulus. This occurs due to a shift in the crystal structure of the piezoceramic materials (e.g., from orthorhombic to cubic, or hexagonal to cubic, etc.). With respect to a piezoceramic ring, such a change in shape results in an internal strain and therefore shrinkage of the disc that results in bending of the disk due to its rigid structure. Because the ring is affixed to the mesh plate, the bending of the ring is transferred to the mesh material. When the electric current is disconnected from the piezoelectric ring, the ring and mesh plate return to their original shape and position. As such, a continuous change of the shape and position will result in an oscillating motion that can be used as a vibration source. In various implementations, the frequency of the piezoelectric ring may be in the range of a few Hz to several MHz. For example, in some implementations the frequency of the piezoelectric ring in in the inclusive range of approximately 50 KHz to approximately 150 KHz, with an average, in one implementation of approximately 110 KHz, in another implementation of approximately 113 KHz, in another implementation of approximately 117 KHz, in another implementation, of approximately 130 KHz, in another implementation, of approximately 150 KHz, in another implementation, of approximately 170 KHz, and in another implementation, of approximately 250 KHz. In other implementations, the frequency of the piezoelectric ring is in the inclusive range of approximately 1 MHz to approximately 5 MHz, with an average of approximately 3 MHz to approximately 3.5 MHz.

In various implementations, a variety of different piezoelectric materials are possible, including natural or synthetic materials. Some non-limiting examples of natural piezoelectric materials include, for example, quartz, berlinite ($AlPO_4$), sucrose, rochelle salt, topaz, tourmaline-group minerals, lead titanate ($PbTiO_3$), and collagen. Some non-limiting examples of synthetic materials include, for example, a ($La_3Ga_5SiO_{14}$), gallium phosphate, gallium orthophosphate ($GaPO_4$), lithium niobate ($LiNbO_3$), lithium tantalate ($LiTaO_3$), AlN, ZnO, barium titanate ($BaTiO_3$), lead zirconate titanate ($Pb[Zr_xTi_{1-x}]O_3$) (a.k.a. PZT), potassium niobate ($KNbO_3$), sodium tungstate ($Na_2WO_3$), $Ba_2NaNb_5O_5$, $Pb_2KNb_5O_{15}$, zinc oxide (ZnO), sodium potassium niobate ($(K,Na)NbO_3$) (a.k.a. NKN), bismuth ferrite ($BiFeO_3$), sodium niobate $NaNbO_3$, barium titanate ($BaTiO_3$), bismuth titanate $Bi_4Ti_3O_{12}$, sodium titanate, and sodium bismuth titanate $NaBi(TiO_3)_2$. In other implementations, polymers exhibiting piezoelectric characteristics may be used, including, but not limited to, polyvinylidene fluoride (PVDF).

In various implementations, a mesh plate of an atomization assembly may be in contact with at least a portion of a liquid composition, and/or may be proximate at least a portion of a liquid composition, and/or may receive (such as via a delivery mechanism) at least a portion of a liquid composition. In such a manner, the resulting vibration of the plate generates an aerosol from the contacted liquid composition. In particular, in some implementations, the liquid composition is driven through the plurality of micro perforations resulting in the generation of a plurality of aerosol particles. Likewise, in other implementations, such as, for example, implementations in which the mesh plate is immersed in the liquid composition, vibration of the plate creates ultrasonic waves within the liquid composition that result in the formation of an aerosol at the surface of the liquid composition. As will be described in more detail below, in other implementations the liquid composition may be applied and/or transferred to the atomization assembly to create the aerosol. In various implementations, the mesh plate may be made of a variety of materials, including for example, one or more metal materials, such as titanium, stainless steel, palladium, nickel, etc., or a polymer material, such as polyimides materials, etc.

Referring back to FIG. 1, in the depicted implementation one or both of the first or second atomization assemblies 115A, 115B may be controlled via the control component 106 and/or the power source 108. In such a manner, control of one or both of the first or second atomization assemblies 115A, 155B may be automatic or on-demand. In some implementations, automatic activation of the first and/or second atomization assemblies may be triggered, for example, by a draw on the device by a user. In some implementations, on-demand activation of the first and/or second atomization assemblies may be activated using an input element, such as, for example, a pressure activated device (e.g., one or more push-buttons). In some implementations, the aerosol delivery device may be configured so that the first and second atomization assemblies operate independently of each other. As such, in some instances of an example implementation, only aerosol comprising the first liquid composition may be delivered to the user, while in other instances of the example implementation, only aerosol comprising the second liquid composition may be delivered to the user, while in still other instances of the example implementation, both aerosol comprising the first liquid composition and aerosol comprising the second liquid composition may be delivered to the user. In still other implementations, a user may be able to adjust the amount of aerosol comprising the first and/or second liquid compositions that is delivered to the user.

In the depicted implementation, the timing of aerosol formation from the first and second atomization assemblies 115A, 155B may differ. For example, in some implementations the first atomization assembly may begin to generate aerosol some period of time after the second atomization assembly begins to generate aerosol. In some implementations, for instance, the first atomization assembly may begin to generate aerosol a fraction of a second (e.g., a half a second) after the second atomization assembly begins to generate aerosol (or vice versa). In other implementations, the difference in time may be more or less than a fraction of second. In still other implementations, the difference between initiation of aerosol generation between the first and second atomization assemblies may not be time-based, but, rather, may be based on a different event, such as, for example, a number of puffs. In some implementations, the second atomization assembly may begin to generate aerosol a few puffs (e.g., 1-5 puffs) before the first atomization assembly begins to generate aerosol (or vice versa). It should be noted that in some implementations, one of the atomization assemblies may generate aerosol several times before the other atomization assembly begins to generate aerosol. For example, in some implementations one of the atomization assemblies may generate aerosol for the first few puffs (e.g., 1-3 puffs), after which both atomization assemblies may generate aerosol one after the other, or at the same time.

In some implementations, the first atomization assembly may be configured to generate a first aerosol from a first liquid composition after the second atomization assembly generates a second aerosol from a second liquid composition, wherein the second liquid composition is different than the first liquid composition and the first aerosol has smaller particle sizes than the second aerosol. In some of such implementations, this may facilitate delivery of the first aerosol to the lungs of a user. For example, if the second liquid composition 112B of the depicted implementation includes phospholipid-based molecules having two ends, one of which is hydrophilic, and the other of which is hydrophobic, due to the hydrophilicity on one end and the larger size of the particles, most of the particles will tend to deposit in the mouth and throat area of a user with their hydrophobic end directed toward the user's air pathway. This early delivery of the phospholipid particles may have certain benefits. For example, in the depicted implementation, the second liquid composition 112B comprises phospholipid-based molecules including a flavorant aerosolized into larger particles that are delivered to the user before a first liquid composition 112A comprising a water-based liquid containing an active ingredient, such as nicotine, aerosolized into smaller particles. In such a manner, the particles from the second liquid composition 112B may deposit in the throat and mouth area of the user, and the hydrophobic ends of the phospholipid molecule may repel the subsequently generated water-based aerosol particles comprising nicotine from the first liquid composition 112A. This may result in increased delivery of particles from the first liquid composition to the lungs of the user.

Figure 4:
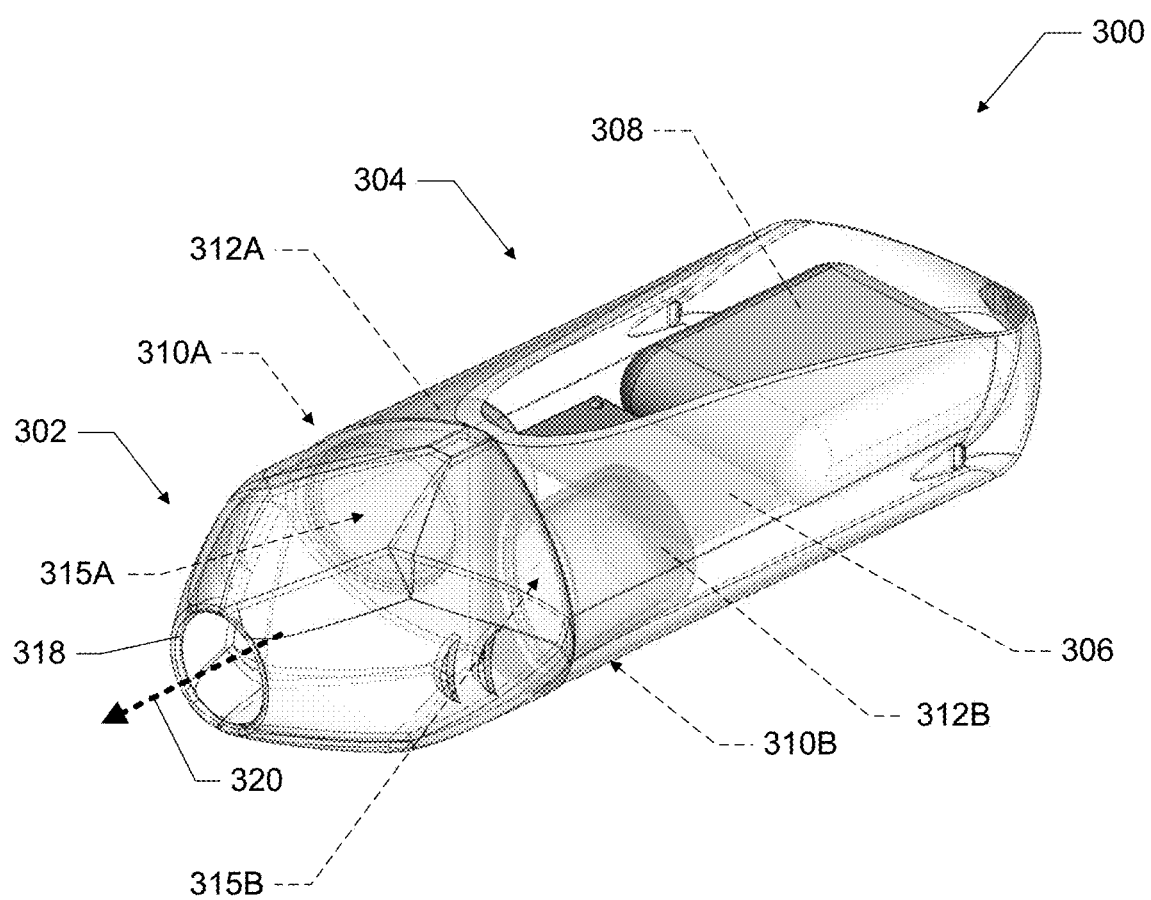
FIG. 4 illustrates a perspective view of an aerosol delivery device, according to an example implementation of the present disclosure.
Figure 5:
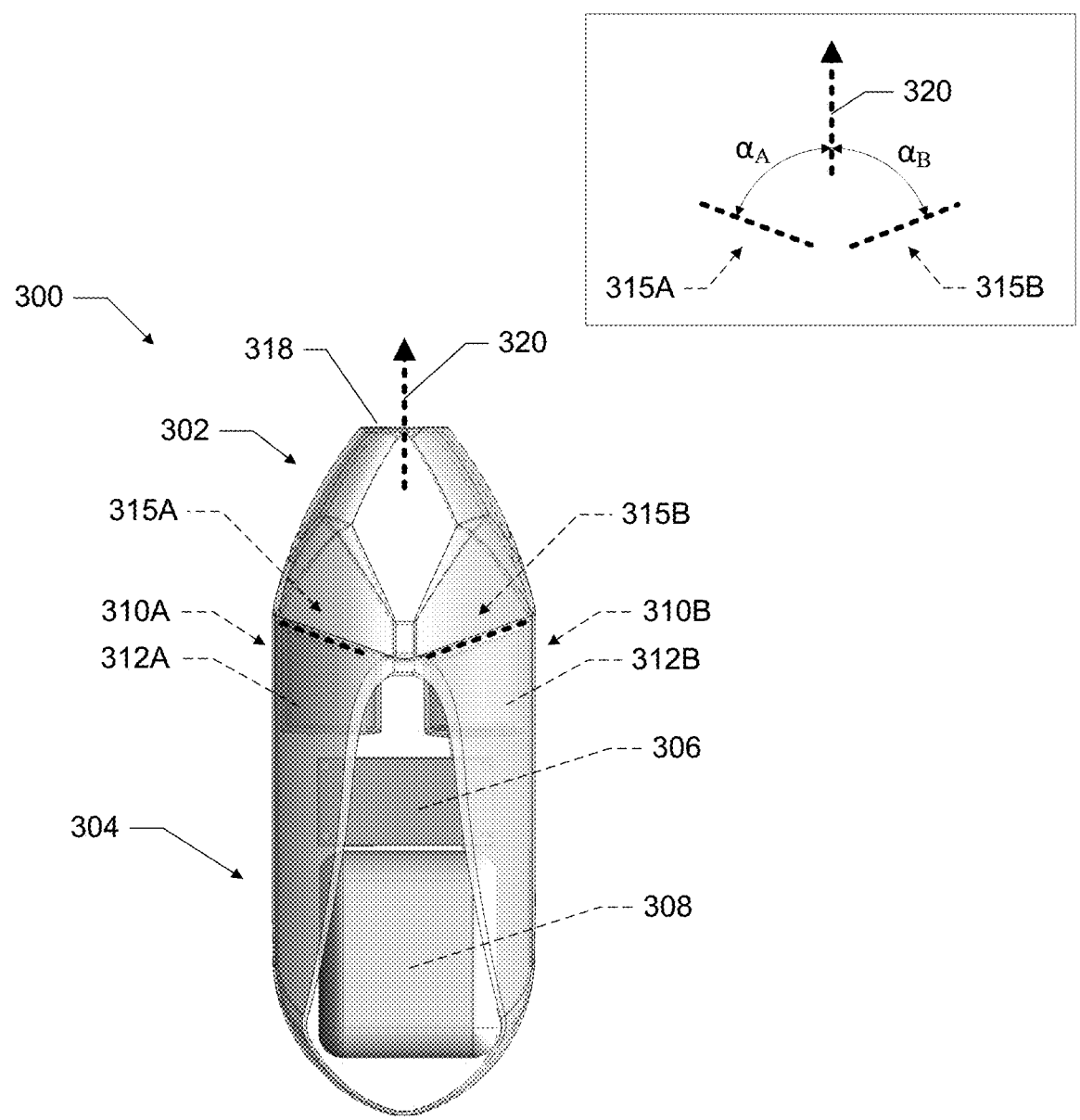
FIG. 5 illustrates a top view of a portion of an aerosol delivery device, according to an example implementation of the present disclosure.

FIG. 4 illustrates an aerosol delivery device, according to another example implementation of the present disclosure, and FIG. 5 illustrates a top view of a portion of the aerosol delivery device of FIG. 4. In particular, FIGS. 4 and 5 illustrate an aerosol delivery device 300 comprising a mouthpiece portion 302 and a housing 304. To aid in the description of the device, certain portions of the housing 304 have been removed. In FIG. 4, the mouthpiece portion 302 and the housing 304 are shown transparent. In FIG. 5, the mouthpiece portion 302 has been removed. In various implementations, the mouthpiece portion 302 may be permanently or detachably aligned in a functioning relationship with the housing 304. In some implementations, for example, the mouthpiece portion and the housing may comprise a single part, whereas in other implementations, a connection therebetween may be releasable such that, for example, the housing and/or the mouthpiece portion) may be reused and/or may be disposable and/or refillable. Reference is made to the above discussion regarding the mouthpiece portion and the housing, as well as configurations and variations thereof. In various implementations, the aerosol delivery device 300 may have a variety of different shapes. Reference is also made to the above discussion regarding possible shapes of the aerosol delivery device.

In specific implementations, one or both of the housing 304 or the mouthpiece portion 302 may be referred to as being disposable or as being reusable. In some implementations, the aerosol delivery device may include a reusable power source. For example, in the depicted implementation the housing 304 includes a control component 306 and a battery 308. In other implementations, other power sources may be used. Reference is made to the above discussion regarding possible power sources, as well as configurations and variations thereof. In the depicted implementation, the control component 306 may comprise a printed circuit board (PCB), an integrated circuit, a memory component, a microcontroller, or the like. Additional components may also be included. Reference is made to the above discussion regarding the control component and other possible components, including sensors, indicators, input elements, etc., as well as configurations and variations thereof.

In the depicted implementation, the housing 304 includes a first liquid reservoir 310A configured to contain a first liquid composition 312A, and a second liquid reservoir 310B configured to contain a second liquid composition 312B. In some implementations, the first and second liquid reservoirs may be part of the housing (such as, for example, comprising a molded feature of the housing), while in other implementations, one or both of the first or second liquid reservoirs may comprise a separate part. In some implementations, an aerosol delivery device of the present disclosure may comprise one or more refillable liquid reservoirs. As such, in some implementations, one or both of the first or second liquid reservoirs may be reusable. Reference is made to the above discussion regarding the housing and/or the first and second liquid reservoirs, as well as configurations and variations thereof. In the depicted implementation, one or both of the first or second liquid compositions 312A, 312B comprises an aerosol precursor composition. Reference is made to the above discussion regarding possible liquid compositions, aerosol precursor compositions, and relative amounts, as well as configurations and variations thereof.

In the depicted implementation, the first liquid reservoir 310A is in fluid communication (either directly or through one or more additional components) with at least a portion of a first atomization assembly 315A. Likewise, the second liquid reservoir 310B of the depicted implementation is in fluid communication (either directly or through one or more additional components) with at least a portion of a second atomization assembly 315B. In some implementations, at least one of the liquid reservoirs 310A, 310B may comprise an independent container (e.g., formed of walls substantially impermeable to the liquid composition). In some implementations, the walls of at least one of the liquid reservoirs may be flexible and/or collapsible, while in other implementations the walls of at least one of the liquid reservoirs may be substantially rigid. In some implementations, at least one of the liquid reservoirs may be substantially sealed to prevent passage of the liquid composition therefrom except via any specific openings or conduits provided expressly for passage of the liquid composition, such as through one or more transport elements as otherwise described herein.

In the depicted implementation, one or more electrical connections connect the atomization assemblies 315A, 315B to the control component 306 and/or the battery 308. In such a manner, the atomization assemblies 315A, 315B of the depicted implementation may be energized by the battery 308 and/or control component 306 (e.g., so as to vibrate a component of the atomization assembly at a relatively high rate). Some examples of electronic/control components that may be applicable to the present disclosure are described in U.S. Pat. App. Pub. No. 2019/0014819 to Sur, which is incorporated herein by reference in its entirety.

In various implementations, the atomization assemblies may be fluidly coupled with respective portions of liquid compositions such that the atomization assemblies generate an aerosol from the respective liquid compositions. In various implementations, the atomization assemblies may be directly fluidly coupled with a portion of the respective liquid compositions, or indirectly fluidly coupled with a portion of the respective liquid compositions, such as via one or more liquid transport elements. Reference is made to the above discussion regarding possible liquid transport elements, as well as configurations and variations thereof.

In some implementations, the liquid composition may be driven through a component of the atomization assembly resulting in the generation of a plurality of aerosol particles. Likewise, in other implementations, vibration of a component of the atomization assembly may create ultrasonic waves within the liquid composition and/or surface acoustic waves in the liquid composition, that result in the formation of an aerosol at the surface of the liquid composition. In some implementations the liquid composition may be applied and/or transferred to a component of the atomization assembly to create the aerosol.

In various implementations, the housing and/or the mouthpiece portion may include one or more air intakes (not shown), which may comprise one or more openings allowing for passage of ambient air into the housing and/or mouthpiece portion. In some implementations, the air intake may draw air into and/or around one or more of the atomization assemblies, where it may be mixed with the vaporized liquid composition to comprise the aerosol that is delivered to the user. It should be noted that in some implementations the air intake need not be adjacent the housing, and, in some implementations, may be located downstream from one or more of the atomization assemblies. As noted, in some implementations, one or more air intakes may be formed through the mouthpiece portion (e.g., such that it does not enter the housing) or some other portion of the aerosol delivery device. It should be noted that some implementations need not include a mouthpiece portion and/or the mouthpiece portion may be integral with the housing.

In some implementations, when a user draws on the device, airflow may be detected by a sensor, and one or both of the atomization assemblies 315A, 315B may be activated, which may vaporize the respective liquid compositions. As noted above, in some implementations drawing upon the mouthend of the device causes ambient air to enter the device. The drawn air may then combine with the formed vapor to form the aerosol. The aerosol may then be whisked, aspirated, or otherwise drawn away from the atomization assemblies and out of an opening 318 in the mouthend of the device, along an aerosol exit path 320. In other implementations, in the absence of an airflow sensor, one or both of the atomization assemblies may be activated manually, such as via one or more push buttons (not shown). Additionally, in some implementations, the air intake may occur through the mouthpiece portion, and/or through the housing, and/or between the mouthpiece portion and the housing. It should be noted that in some implementations, there may be one or more components between one or both of the atomization assemblies and the opening in the mouthend of the device. For example, in some implementations one or more heating components may be located downstream from either or both of the atomization assemblies. In various implementations, a heating component may comprise any device configured to elevate the temperature of the generated aerosol, including, for example, one or more coil heating components, ceramic heating components, etc.

In various implementations, one or both of the atomization assemblies may comprise a variety of different components or devices configured to generate an aerosol from the liquid composition. For example, in some implementations the atomization assembly may comprise a jet nebulizer assembly, which may be configured to utilize compressed air to generate an aerosol. In other implementations, the atomization assembly may comprise an ultrasonic assembly, which may be configured to utilize the formation of ultrasonic waves within the liquid composition to generate an aerosol. In other implementations, the atomization assembly may comprise a vibrating mesh assembly, which may comprise a piezoelectric material (e.g., a piezoelectric ceramic material) affixed to and substantially surrounding a mesh plate, (e.g., a perforated plate such as a micro-perforated mesh plate) that is vibrated within the liquid composition or proximate the surface of the liquid composition to generate an aerosol. In still other implementations, the atomization assembly may comprise a surface acoustic wave (SAW) or Raleigh wave assembly, which may utilize surface wave characteristics to generate an aerosol at the surface of the liquid composition. It should be noted that for purpose of this application, an ultrasonic assembly may be any assembly configured to create ultrasonic waves within the liquid composition. In some implementations, for example, a vibrating mesh assembly may also operate as an ultrasonic assembly. Reference is made to the above discussion regarding possible atomization assemblies, as well as configurations and variations thereof.

Although in other implementations the first and second atomization assemblies may be substantially co-linear and/or substantially parallel to each other, in the depicted implementation the first and second atomization assemblies 315A, 315B are angled with respect to each other. In particular, the first atomization assembly 315A and the second atomization assembly 315B of the depicted implementation are angled toward each other and the aerosol exit path 320. Although in other implementations the first and second atomization assemblies may have a variety of different configurations, in the depicted implementation the first and second atomization assemblies 315A, 315B have an overall substantially planar shape, with each atomization assembly 315A, 315B including a surface that forms an angle with respect to the aerosol exit path 320 such that the aerosol formed thereby is directed to the aerosol exit path 320. In various implementations, the angle formed by the first or second automation assembly with respect to the aerosol exit path may vary (e.g., between 0 degrees and 180 degrees), and in some implementations the first and second atomization assemblies may form different angles with respect to the aerosol exit path. In the depicted implementation, the first atomization assembly 315A forms an angle $\alpha_A$ with respect to the aerosol path 320, and the second atomization assembly 315B forms an angle $\alpha_B$ with respect to the aerosol exit path 320. Although other configurations are possible, in the depicted implementation, the angles $\alpha_A$ and $\alpha_B$ are substantially the same, and are greater than 45 degrees and less than 180 degrees, and in particular, less than 90 degrees.

In the depicted implementation, the first reservoir 310A contains a first liquid composition 312A, and the second reservoir 310B contains a second liquid composition 312B, wherein the first liquid composition 312A is different than the second liquid composition 312B. In addition, the first atomization assembly 315A is configured generate a first aerosol having a first particle size, and the second atomization assembly 315B is configured to generate a second aerosol having a second particle size, wherein the first particle size is different than the second particle size. Reference is made to the above discussion regarding the first and second liquid compositions, the first and second atomization assemblies, the respective aerosol particle sizes, and the timing thereof, as well as configurations and variations thereof.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:
a housing defining an outer wall, and further including a power source and a control component;
a first reservoir located in the housing configured to contain a first liquid composition;
a second reservoir located in the housing configured to contain a second liquid composition;
a first atomization assembly located in the housing configured to vaporize the first liquid composition to generate a first aerosol; and
a second atomization assembly located in the housing configured to vaporize the second liquid composition to generate a second aerosol,
wherein at least one of the first and second atomization assemblies comprises a piezoelectric ring affixed to and substantially surrounding a mesh plate.

2. The aerosol delivery device of claim 1, wherein both the first and second atomization assemblies comprise a respective piezoelectric ring affixed to and substantially surrounding a mesh plate.

3. The aerosol delivery device of claim 1, wherein the mesh plate of one of the first and second vibrating assemblies is substantially flat.

4. The aerosol delivery device of claim 1, wherein at least a portion of the mesh plate of one of the first and second vibrating assemblies is convex with respect to the respective reservoir.

5. The aerosol delivery device of claim 1 further comprising a mouthpiece portion located proximate to or on the housing that defines an aerosol exit path.

6. The aerosol delivery device of claim 5, wherein the mouthpiece portion is configured to be removable and replaceable from the housing.

7. The aerosol delivery device of claim 5, wherein the first and second reservoirs are located on opposite sides of the aerosol exit path.

8. The aerosol delivery device of claim 5, wherein a surface of each of the first and second atomization assemblies forms an angle with respect to the aerosol exit path.

9. The aerosol delivery device of claim 8, wherein the angle formed between a least one of the first and second atomization assemblies with respect to the aerosol exit path is a substantially right angle.

10. The aerosol delivery device of claim 8, wherein the angle formed by a surface of at least one of the first and second atomization assemblies is greater than 45 degrees and less than 180 degrees.

11. The aerosol delivery device of claim 8, wherein the angle formed by a surface of each of the first and second atomization assemblies is greater than 45 degrees and less than 180 degrees.

12. The aerosol delivery device of claim 1, wherein the first aerosol has a first particle size, and the second aerosol has a second particle size.

13. The aerosol delivery device of claim 12, wherein the first particle size is smaller than approximately 4 microns.

14. The aerosol delivery device of claim 12, wherein the second particle size is larger than approximately 4 microns.

15. The aerosol delivery device of claim 12, wherein the second particle size between approximately 4 microns and approximately 15 microns.

16. The aerosol delivery device of claim 1, wherein the first and second atomization assemblies are configured to generate the first and second aerosols substantially simultaneously.

17. The aerosol delivery device of claim 1, wherein the first atomization assembly is configured generate the first aerosol after the second atomization assembly is configured to generate the second aerosol.

18. The aerosol delivery device of claim 1, wherein the first and second atomization assemblies are configured to be automatically controlled via the control component.

19. The aerosol delivery device of claim 1, wherein at least one of the first and second liquid compositions comprises a water-based liquid that includes nicotine.

20. The aerosol delivery device of claim 1, wherein at least one of the first and second liquid compositions includes a pulmonary surfactant.

* * * * *